United States Patent [19]

Cummings et al.

[11] Patent Number: 4,931,057
[45] Date of Patent: Jun. 5, 1990

[54] COMPRESSION ANASTOMOSIS COUPLING ASSEMBLY

[75] Inventors: Joel W. Cummings, Hasbrouck Heights, N.J.; Ionel E. Teodorescu, Woodside, N.Y.

[73] Assignee: Pfizer Hospital Products Group, Inc., New York, N.Y.

[21] Appl. No.: 174,571

[22] Filed: Mar. 29, 1988

[51] Int. Cl.⁵ .............................................. A61B 17/00
[52] U.S. Cl. .................................................... 606/153
[58] Field of Search .............. 128/334 R, 334 C, 335, 128/337, 346; 227/DIG. 1; 411/509, 457, 908, 918, 432, 433; 24/621, 297, 295, 615, 616, 590, 598

[56] References Cited

U.S. PATENT DOCUMENTS

| | | | |
|---|---|---|---|
| 874,957 | 12/1907 | Godley | 24/615 |
| 1,480,746 | 10/1921 | DeBie | 411/457 |
| 4,055,186 | 10/1977 | Leveen | 128/334 C |
| 4,154,241 | 5/1979 | Rudie | 128/334 C |
| 4,467,804 | 8/1984 | Hardy et al. | 128/334 C |
| 4,552,148 | 11/1985 | Hardy, Jr. et al. | 128/334 C |
| 4,567,891 | 2/1986 | Kanshin et al. | 128/334 C |
| 4,598,712 | 8/1986 | Rebuffat et al. | 128/334 C |
| 4,657,019 | 4/1987 | Walsh et al. | 128/334 C |
| 4,681,108 | 7/1987 | Rosati et al. | 128/334 R |

Primary Examiner—Randall L. Green
Assistant Examiner—Gary Jackson
Attorney, Agent, or Firm—Peter C. Richardson; Lawrence C. Akers; John L. LaPierre

[57] ABSTRACT

A compression anastomosis assembly of interlocking coupling members, particularly suitable for use in achieving anastomosis of tubular organs, having an improved locking feature to prevent inadvertent disassembly of installed coupled members. The design and configuration of the members also provide for ease in placement of the assembly in a living body wherein preferably one assembly member includes a cutting guide and a cutting ring which facilitate use of a cutting implement commonly associated with a device suitable for use during assembly implantation.

26 Claims, 8 Drawing Sheets

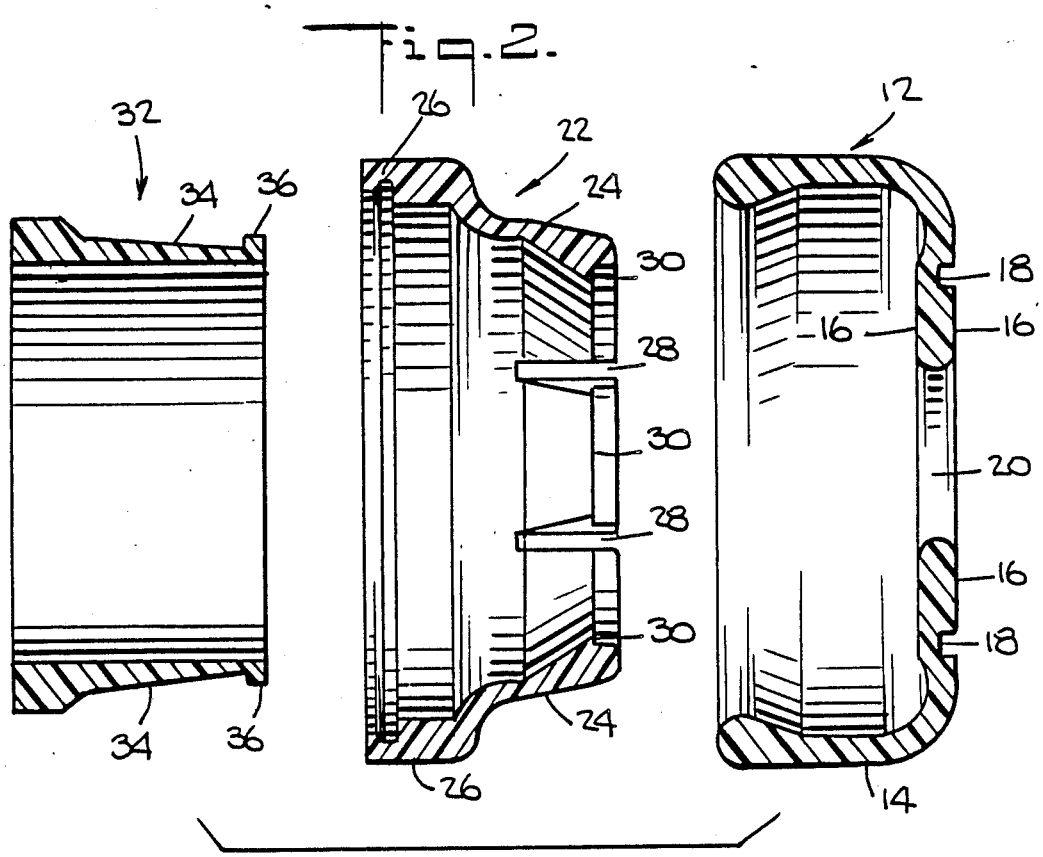
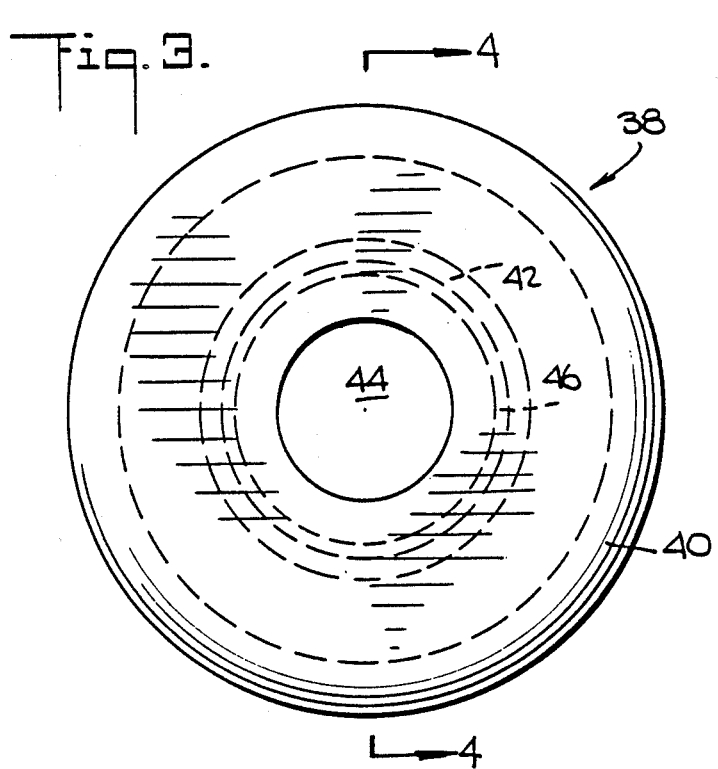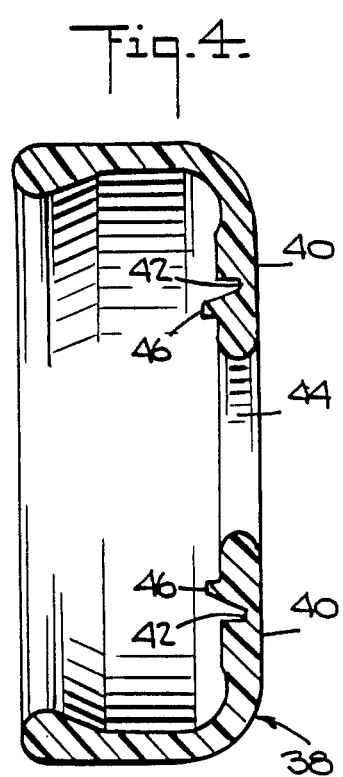

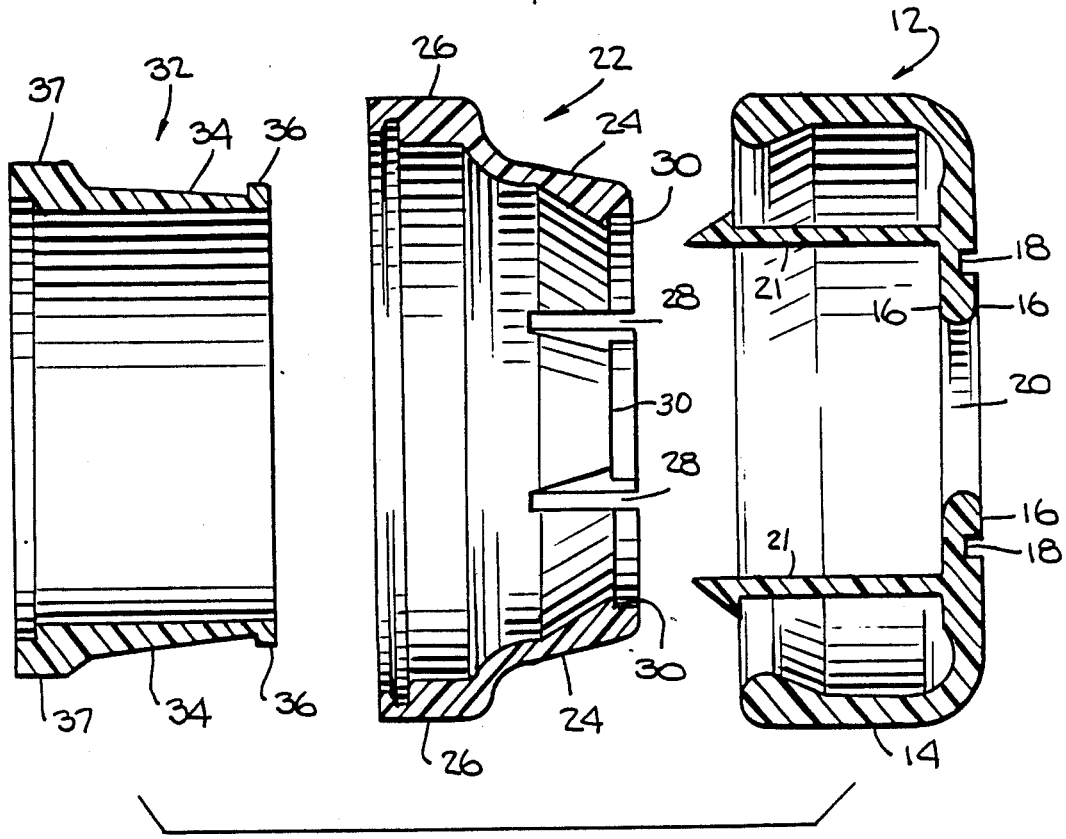

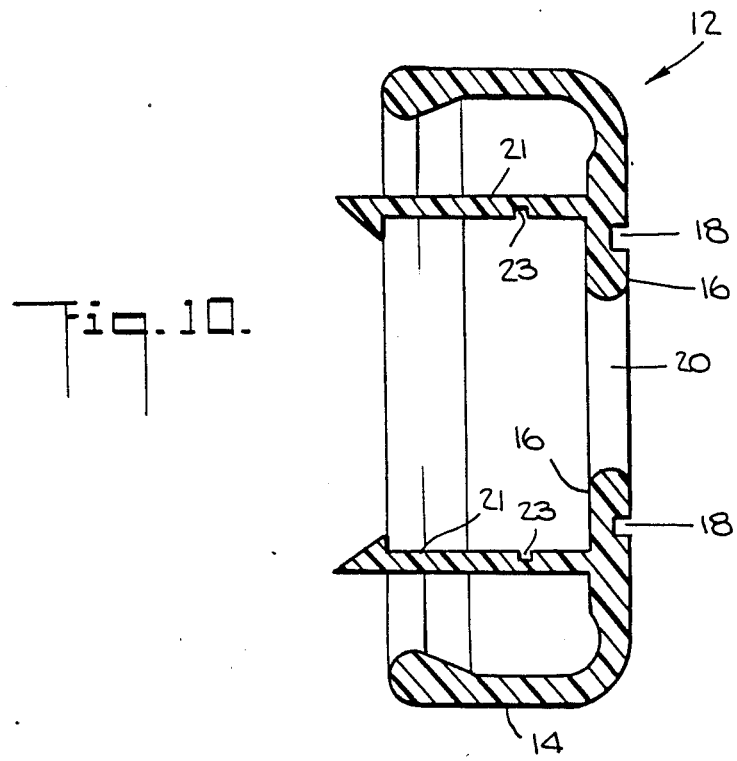
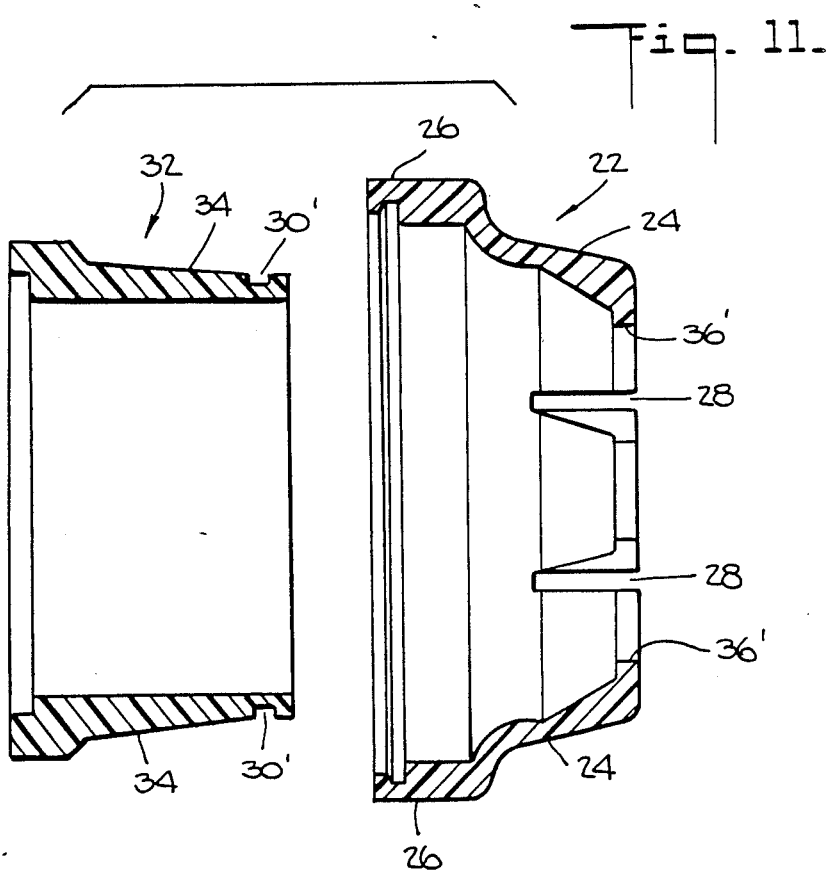

Fig. 12.
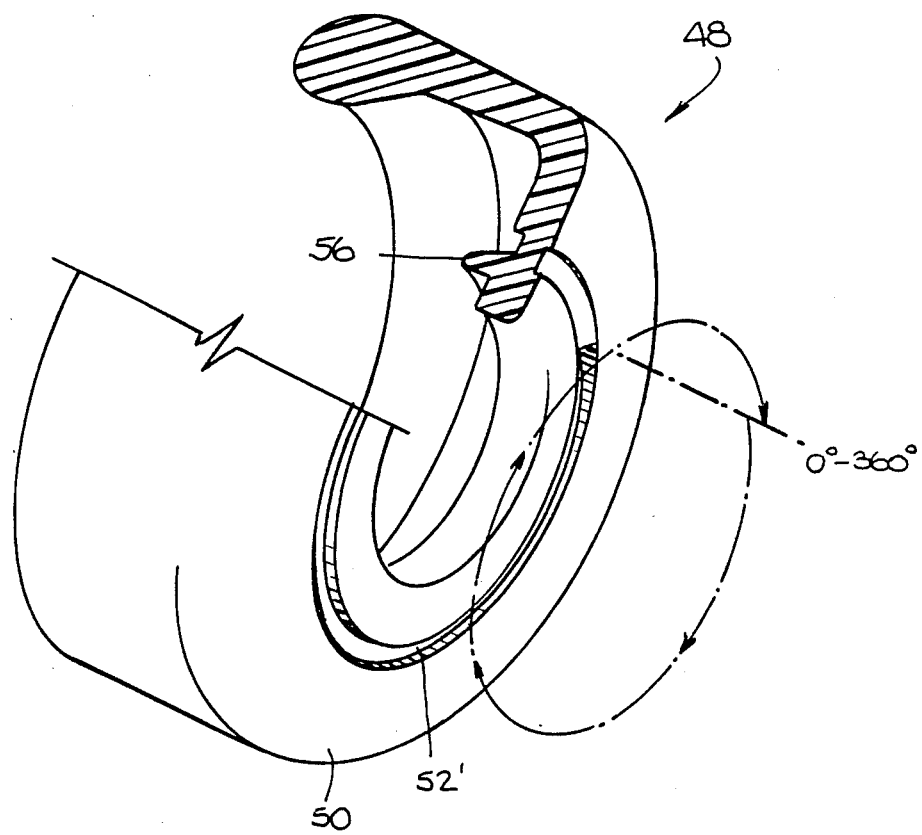
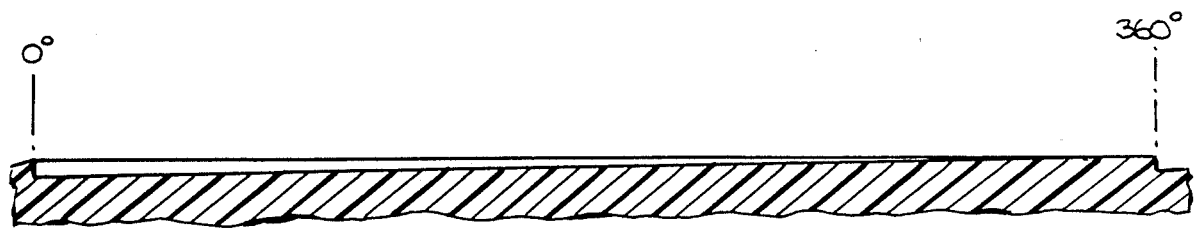
Fig. 13.

COMPRESSION ANASTOMOSIS COUPLING ASSEMBLY

BACKGROUND OF THE INVENTION

The present invention generally relates to anastomosis of living tissue and, more particularly, it relates to an assembly of interlocking coupling members used for compression anastomosis of tubular structures. The assembly has an improved locking feature which prevents inadvertent member dislocation after installation of a coupled assembly in a body. Also contemplated by the invention are various coupling member configurations which will facilitate placement of the assembly in a patient and enhance in the removal of a surgical instrument typically used in positioning the assembly in the patient.

A compression anastomosis coupling assembly of the type herein disclosed is typically used when a segment of a colon, or like tubular structure, is to be resected. After a section of the colon is removed, leaving opposed, proximal and distal, free ends, the coupling members are introduced, aligned and brought into locking engagement. The assembly, however, is equally suitable for use in surgical operations for connecting tubular structures in other than end to end orientation, namely, the assembly could be used to achieve either an end to side or a side to side tubal connection. The coupled members capture and compress the free ends of the colon together to effect an anastomosis by holding tissue in compression until healing occurs. Blood supply to the captured tissue is restricted. Necrosis takes place in the area of the colon captured within the assembly without causing excessive inflammation and trauma. Thereafter, the coupled assembly detaches from the anastomotic site and is expelled spontaneously through the rectum. After assembly expulsion, the colon provides an open passageway at the anastomotic site substantially as that which existed before resectioning.

Disclosure of another device used for circular anastomosis of hollow organs can be found in U.S. Pat. No. 4,598,712. This device advanced the known art field by introducing a new technique for compression anastomosis of hollow organs which, in the majority of cases, had previously been performed by using mechanical staplers for connecting tissue edges by means of metallic staples. Specifically, this device includes a three member coupling assembly having a rear locking feature wherein the inner coupling member of the device includes a conical portion which locks at the base of the intermediate coupling member locking the elements of the device. The present compression anastomosis coupling assembly further advances the art field by introducing a forward or inner locking feature in place of the known rear locking feature. The rear lock, while secure, provides a single locking arrangement whereas the forward lock provides a multiple fastening arrangement. In the forward locking configuration, the integrity of the coupled assembly is further enhanced since forces are equally distributed around the locking circumference and the locking force increases as the assembly is subjected to external forces. In yet another improved locking arrangement, there is a mechanical locking directly between each of the three coupling members. An additional feature of the new assembly which is an improvement over the known device relates to the enhanced ease in placement of the assembly in a patient. Typically, a surgical instrument, having a cutting element for cutting a member of both the known and the new devices, is commonly used with each assembly during implantation. However, the outer element of the known device does not provide a cutting guide mechanism for guiding the cutting element during device installation. The new and improved assembly includes a cutting guide on a face of one of the coupling members. Additionally, while the known device provides a cutting ring or recess on the outer element to help reduce the forces necessary to achieve cutting, the new device further reduces the required cutting forces by changing the configuration of the coupling member through which the cutting element must pass.

The primary objective of the present invention is to further advance the art field by providing a compression anastomotic coupling assembly which is an improvement over existing devices. Accordingly, herein disclosed is an implantable device which is designed and configured for greater ease in installation and which will exhibit a superior in place locking feature during healing at the site of anastomosis and thereafter be naturally expelled intact by the patient.

SUMMARY OF THE INVENTION

The device of the present invention is a novel assembly for compression anastomosis of a tubular structure. The assembly includes first, second and third coupling members, each being biocompatible and each being generally a hollow open cylinder, with the first coupling member being dimensioned and configured to receive therein at least a portion of the second coupling member and with the second coupling member being dimensioned and configured to receive therein at least a portion of the third coupling member. A locking feature included on the second coupling member is adapted for locking coaction with complementary means disposed proximate a first end of the third coupling member. With each coupling member being aligned and urged into engagement, the third coupling member forces the second coupling member into locking engagement with the first coupling member, and the first end of the third coupling member mechanically locks within the second coupling member, thereby effecting an assembly of interlocking coupling members.

In one form of the assembly of the invention, the coupling members are generally thin wall hollow open cylinders with the second and third members having open ends and the first member having one open end and another end having a surface. The locking feature might include a land on the second coupling member coacting with a complementary projection on the third coupling member. Alternatively, the land might be on the third coupling member and the projection on the second coupling member. This form of the invention might also include a recess disposed in the surface and a means for guiding a cutting instrument adapted for usage with the assembly during assembly installation. Also contemplated is a coupling element disposed on the inner face of the surface of the first coupling member for latching engagement with an instrument adapted for usage during assembly implantation in a patient.

In another form of the assembly of the invention, the assembly comprises a first coupling member being generally a thin wall hollow cylinder having first and second ends with the second end being open and the first end having a surface with an axial port. The assembly also includes a second coupling member being generally a thin wall hollow cylinder having open first and second ends and including a first portion having one or more openings disposed in the wall. Additionally, the assembly includes a third coupling member being generally a thin wall hollow cylinder having open first and second ends. The first coupling member is dimensioned and configured to receive therein the first portion of the second coupling member with the second coupling member being dimensioned and configured to receive therein at least a portion of the third coupling member. A means, disposed on the first portion of the second coupling member, is adapted for locking coaction with complementary means disposed proximate a first end of the third coupling member. With each coupling member being aligned and urged into engagement, the third coupling member forces the first portion of the second coupling member into locking engagement with the first coupling member, with the first end of the third coupling member mechanically locking within the first portion of the second coupling member, thereby effecting an assembly of interlocking coupling members. As aforesaid with respect to one form of the invention, this form of the invention might also include like locking and cutting guide features. Also contemplated within the scope of this form of the invention is a recess which might be located on either the inner or the outer face of the surface. Furthermore, the recess might comprise either one or more continuous channels which might follow either a spiral or an angular path. Lastly, the surface of the first coupling member might include one or more openings disposed therein forming a spoke-like configuration.

In yet another form of the assembly of the invention, the assembly includes a direct mechanical lock between first and third coupling members, locating second coupling member therebetween, effecting an assembly locking the three coupling members together as a unit. Furthermore, a second locking feature, directly locking the second and third coupling members to one another, might also be included.

The various features of novelty which characterize the invention are pointed out with particularity in the claims annexed to and forming a part of this disclosure. For a better understanding of the invention, its operating advantages and specific results obtained by its use, reference should be made to the corresponding drawings and descriptive matter in which there is illustrated and described typical embodiments of the invention.

BRIEF DESCRIPTION OF THE DRAWINGS

FIG. 2 is an enlarged exploded axial cross-sectional view of each coupling member of the assembly depicted in FIG. 1.

FIG. 2A is a view much like that depicted in FIG. 2 showing a modified coupling member assembly.

FIG. 3 is an enlarged top plan view of a modified coupling member similar to the rightmost member shown in FIG. 1.

FIG. 4 is a cross-sectional view taken along line 4—4 of FIG. 3.

FIG. 10 schematically represents a modification of the rightmost coupling member shown in FIG. 2A.

FIG. 11 schematically depicts a modified version of the middle and left coupling members illustrated in FIG. 2.

FIG. 12 is a view like that of FIG. 5 but showing a spiral pathway located in a recess in the coupling member.

FIG. 13 is a developed view of the sprial depicted in FIG. 12.

DETAILED DESCRIPTION OF THE PREFERRED EMBODIMENTS

Figure 1:
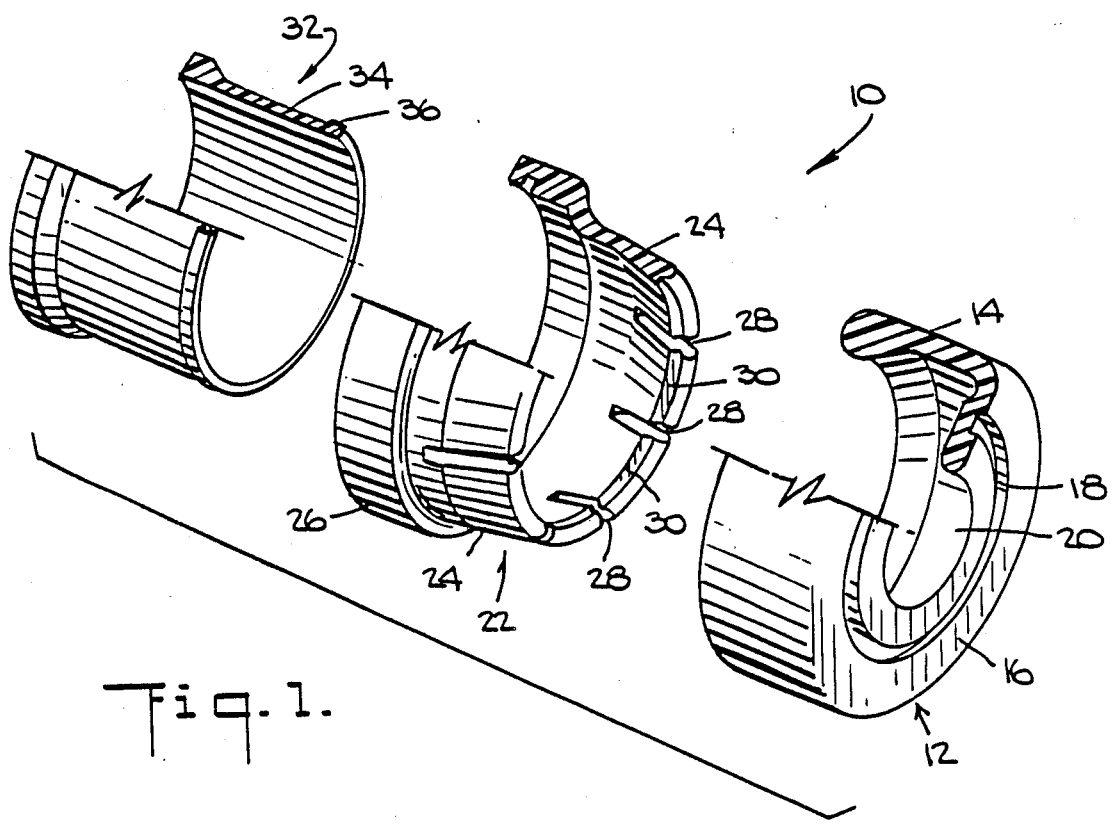
FIG. 1 is an exploded perspective cutaway representation of a compression anastomosis coupling assembly, in accordance with the principles of the present invention, illustrating an embodiment of coupling members prior to interlocking assembly.

The description herein presented refers to the accompanying drawings in which like reference numerals refer to like parts throughout the several views. First turning to FIGS. 1 and 2, there is illustrated an exploded perspective cutaway view and an enlarged exploded axial cross-sectional view, respectively, of assembly 10 of the present invention. The assembly includes a first coupling member 12 having wall 14, surface 16, recess 18, and axial port 20; a second coupling member 22 having first portion 24 and second portion 26 with portion 24 having at least one opening 28 and land 30; and a third coupling member 32 having wall 34 and projecting portion 36. Recess 18, in this embodiment, is located in the outer face of surface 16 of member 12 and recess 18 is a continuous channel. The inner face of surface 16 is that face being in juxtaposition with coupling member 22. While land 30 is shown to be located on portion 24 of coupling member 22 and projection 36 is shown located on coupling member 32, it should be understood and contemplated to be within the scope of the invention, that the locations of the land and projection could be interchanged.

Coupling member 12 is illustrated as having an annular recess 18 and an axial port 20. It should be understood that other recess configurations are also contemplated to be within the scope of the invention. Likewise, that while member 12 has an axial port, it is also contemplated that surface 16 of member 12 be continuous, namely, not include an axial opening. Lastly, although not shown, it is also contemplated that means, for example, a snap ring or a plug, could be included on the inner face of surface 16 to achieve a latching engagement between coupling member 12 and a mating ring or socket included on an instrument adapted for usage during member installation. Other comparable coupling means could also be employed.

As can best be seen in FIG. 2, the coupling members are in coaxial alignment for coupling. The coupling members are dimensioned and configured so that member 12 is adapted to first receive therein portion 24 of member 22 and member 22 is adapted to then receive therein a portion of member 32. Portion 24 of member 22 is constructed of a resilient material so that during coupling, as member 32 slidingly advances within member 22, portion 24 is expanded circumferentially until projection 36 reaches land 30, after which, portion 24 snaps partially back to interlock projection 36 and land 30. Member 32 is now locked against rearward retreat. Cutaway sections 28 enhance the expansion of portion 24 during advancement of member 32 within member 22. The configuration of the inner surface of wall 14 of member 12 is such that it captures expanded portion 24 of member 22 therewithin. Thus, the three coupling members effect an assembly of interlocking coupling members after the forcing of portion 24 into engagement with member 12 and the locking coaction of projection 36 and land 30 mechanically locking members 22 and 32 at a location within portion 24.

FIG. 2A depicts a view substantially as that depicted in FIG. 2. Coupling member 12 has been modified to include projecting segment 21. It should be understood that segment 21 might be a continuous circular member or it might include a plurality of downward projections. Segment 21 might latch about second portion 26 of member 22, passing between members 22 and 32, or about base portion 37 of member 32, passing through the interior of member 32. Member 32 might mechanically lock within first portion 24 of member 22 as aforesaid to provide a second locking feature. Alternatively, member 32 might extend through member 22 and fasten to member 12 at any number of locations along segment 21 by suitable means, for example, projection 36 might be located in a recess or a land (both of which are not shown) along segment 21, to name but two possibilities. Other comparable mechanical coupling means for directly joining members 12 and 32 are deemed to be within the scope of the present invention.

Turning to FIGS. 3 and 4, there is shown an alternate construction of a member like coupling member 12, here designated as 38. Coupling member 38 includes surface 40, recess 42, axial opening 44, and cutting guide rib 46. Recess 42 is like recess 18 except that recess 42 is located on the inner face of surface 40. Surface 40 and axial opening 44 are like surface 16 and axial port 20 shown in FIG. 2. Cutting guide rib 46 on inner face of surface 40 provides a means for guiding a cutting instrument, such is the type shown in FIG. 8 and identified as 86, for usage with the assembly during assembly installation. It should be understood that a cutting guide rib could also be provided on the inner face of surface 16 of coupling member 12 and also function therein as a guide for a cutting implement. It should further be understood that an annular bevel (not shown) could replace cutting guide rib 46 and provide a comparable cutting guide function.

Figure 5:
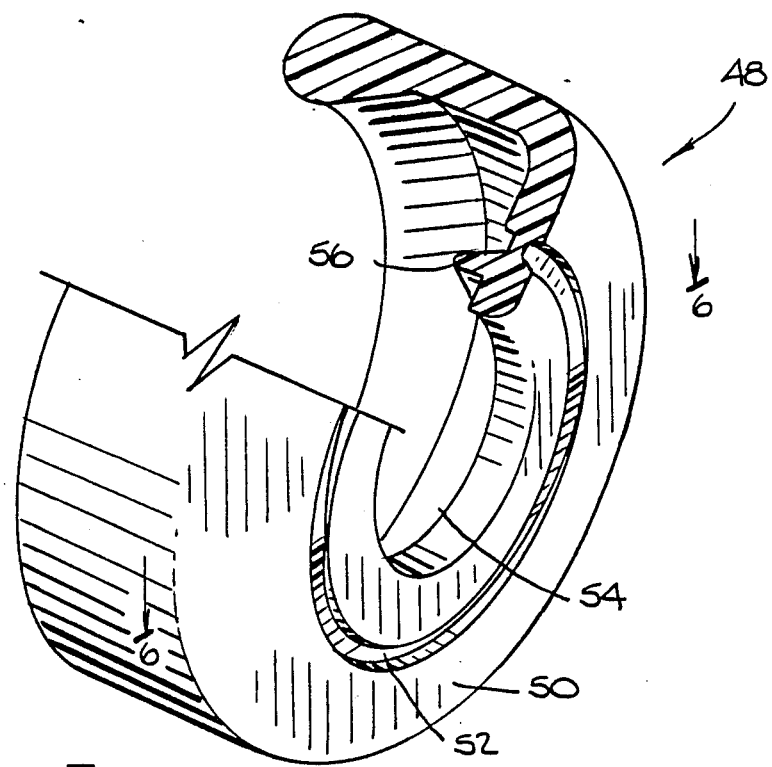
FIG. 5 is an enlarged perspective cutaway view of another modified coupling member similar to the rightmost member shown in FIG. 1.
Figure 6:
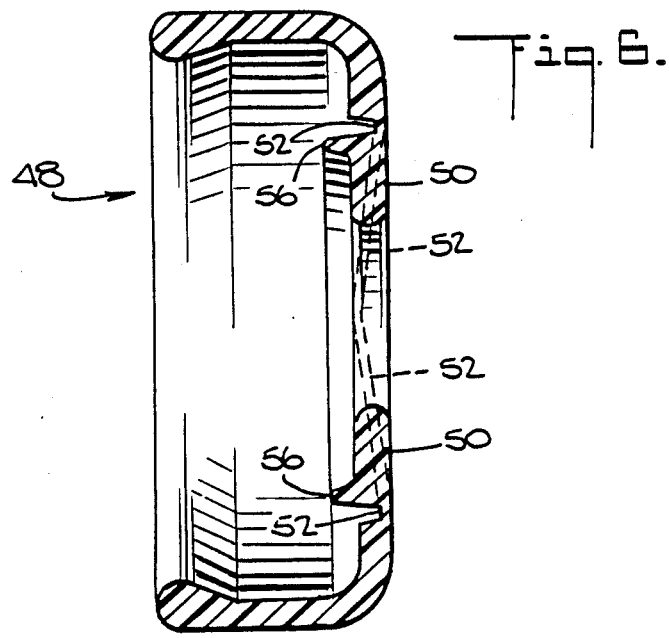
FIG. 6 is an axial cross-section view taken along line 6—6 of FIG. 5.

Turning now to FIGS. 5 and 6, there is shown another alternate construction of a member somewhat like coupling members 12 and 38, here designated as 48. Coupling member 48 includes surface 50, recess 52, axial opening 54, and cutting guide rib 56. The primary distinction in this embodiment is that the configuration of recess 52 follows a number of angular paths. Not shown but also contemplated within the scope of the invention is a recess that follows a spiral path. The remaining member features are like those shown in respect to members 12 and 38.

Figure 7:
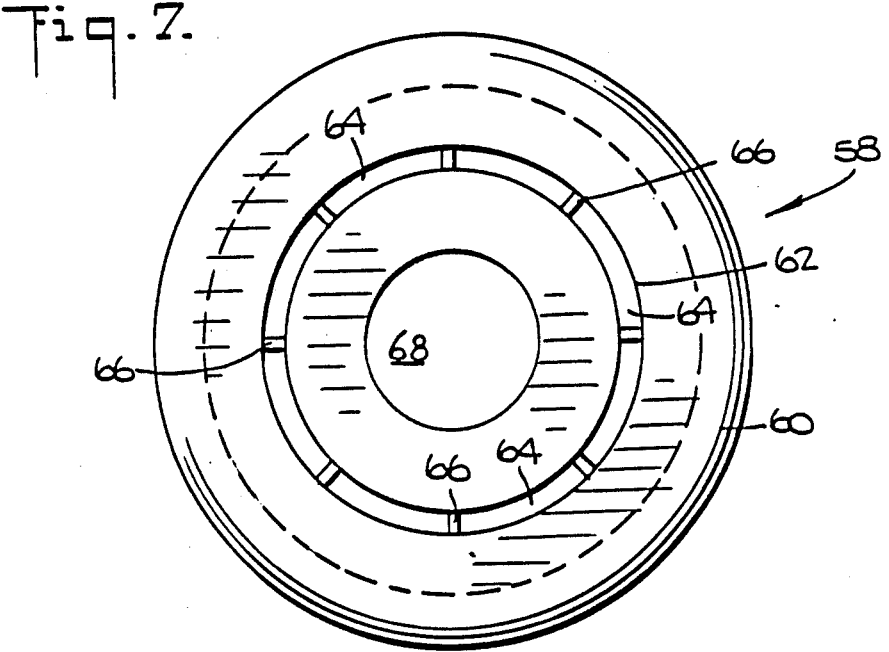
FIG. 7 is a top plan view of yet another modified coupling member similar to the member depicted in FIG. 3.

FIG. 7 shows yet another alternate construction of a member like members 12, 38 and 48, here designated as 58. Coupling member 58 includes surface 60, cutting ring 62 having openings 64 and spokes 66, and axial port 68. Coupling member 58 might also include a cutting guide rib (not shown) much like rib 46, 56. Throughout the many views a recess has been included in the first coupling member. The terms recess and cutting ring could often be used interchangably, that is, at least when the recess assumes an annular shape. An advantage of a cutting ring having a spoke-like configuration is that openings 64 form passageways to allow the escape of gases during member installation. Additionally, with the removal of material from surface 60, lesser operating forces will be required during cutting of member 58 as the assembly is placed in a patient. It should readily be understood that each of coupling members 12, 38, 48 and 58 are suitable for use with coupling members 22 and 32.

The forward or inner locking feature herein provided, namely, the mechanical locking of members 22 and 32 engaging at 30, 36, provides a more secure locking arrangement than that found wherein members lock at a rear location. A rear locking feature, namely, at the base of member 22 where it contacts the base of member 32, is a single locking arrangement about the base whereas the inner locking feature provides a multiple locking arrangement, that is, a separate lock at each location where land 30 and projection 36 meet. This multiplicity of locking feature exists because land 30 is circumferentially interrupted by slots 28 disposed in wall 24 and each land and projection meeting provides an independent locking engagement. The forward locking feature prevents the innermost member 32 from backing out when force is applied to the assembly and, since the force is equally distributed around the locking circumference, the integrity of the coupled assembly is enhanced because the locking force increases as the assembly is subjected to external forces. The various recess or cutting ring configurations of coupling members 38, 48 and 58 provide the advantage of reducing the cutting forces necessary during member installation to cut through the face of the coupling member by reducing the surface area and thickness the cutting edge is cutting against. The cutting guide ring, suitable for inclusion in any of coupling members 12, 38, 48 and 58, provides the additional advantage of consistency of operation by allowing the cutting edge to follow a specified path.

Figure 8:
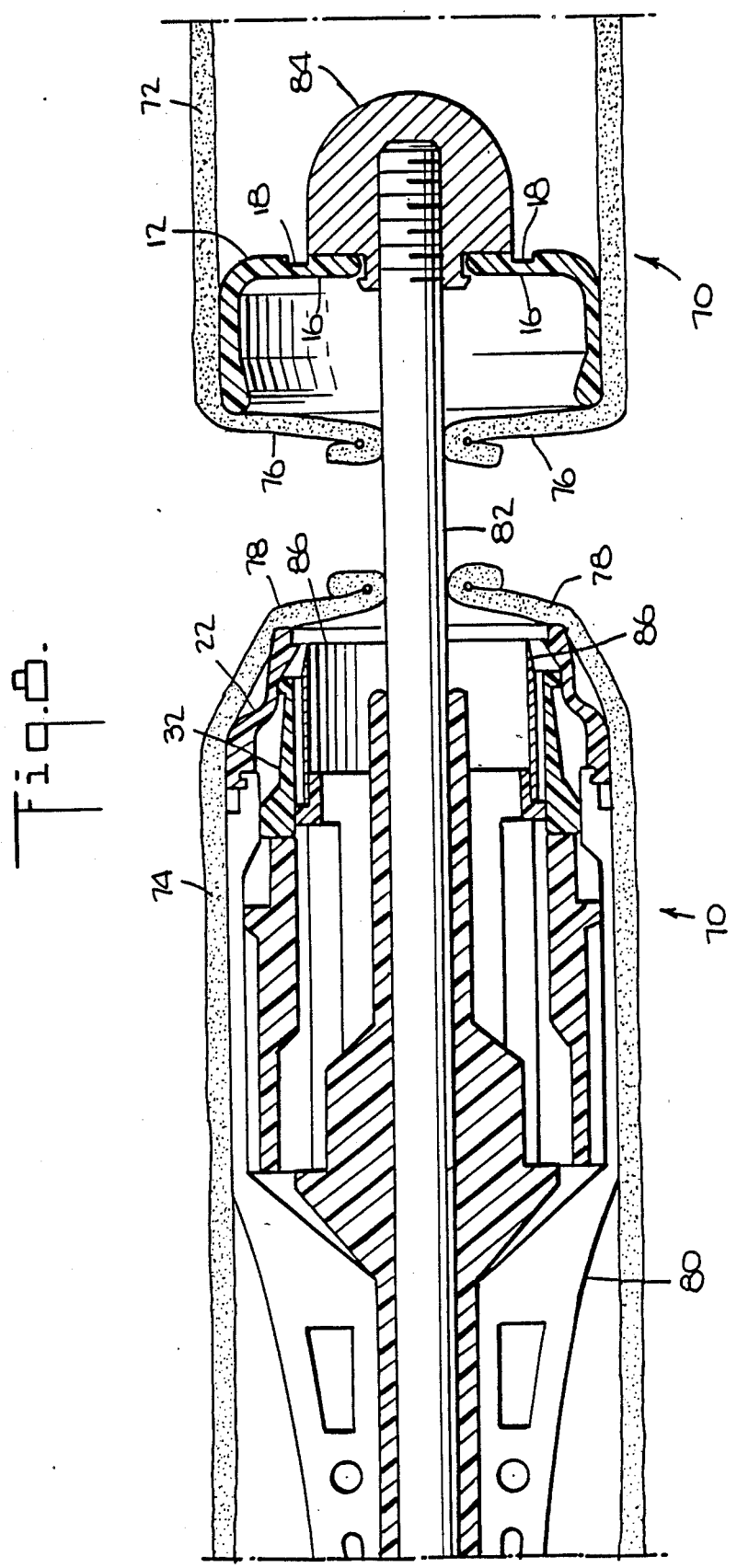
FIG. 8 is a schematic sectional representation of the coupling members, including a surgical instrument used during implantation, being located in free ends of a sectioned colon but before the members are moved into locking engagement.
Figure 9:
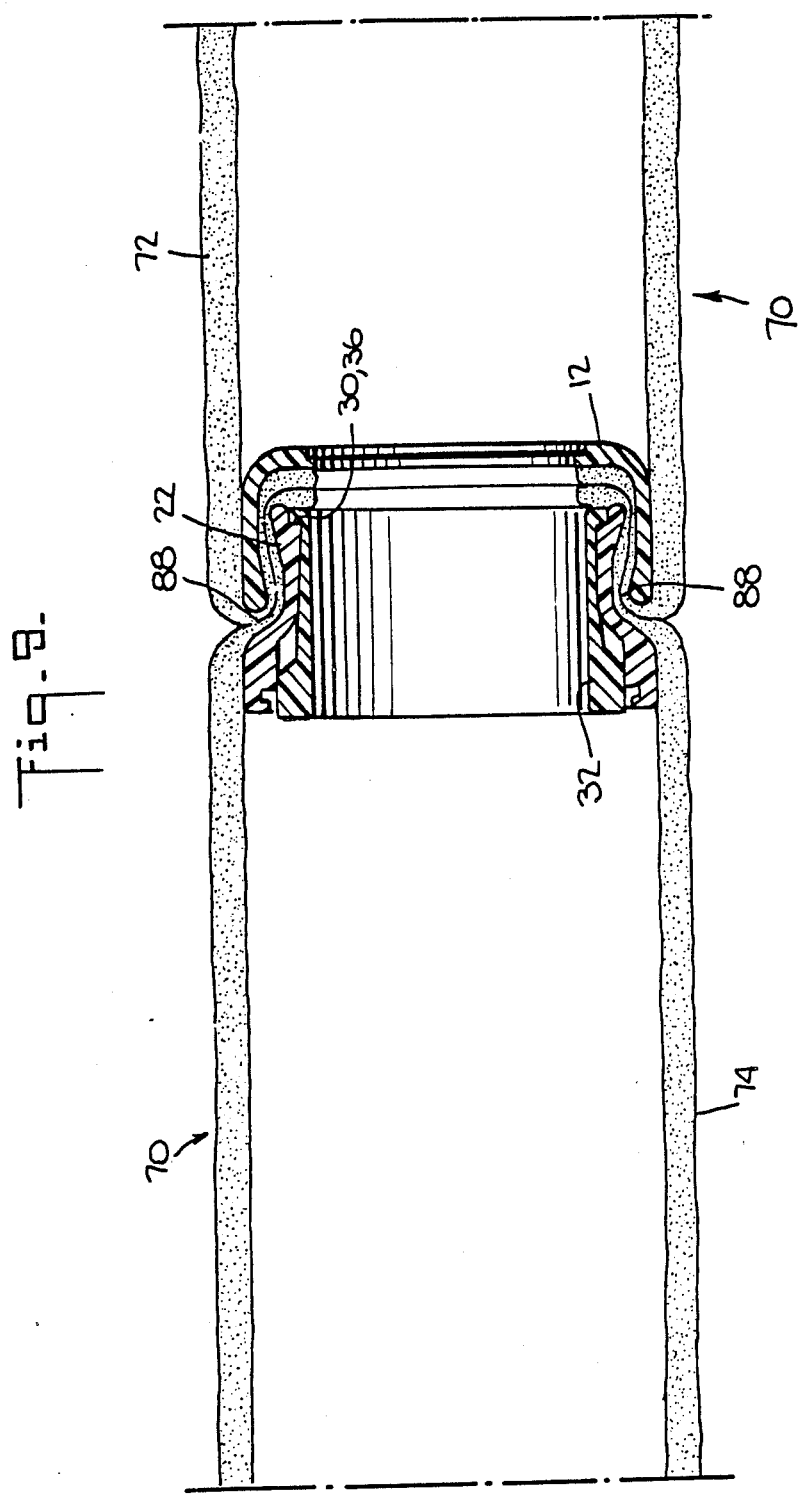
FIG. 9 is a schematic sectional representation similar to that illustrated in FIG. 8 and showing an implanted coupled assembly, capturing and compressing together the free ends of the colon, which will hold the colonic tissue in place until the anastomosis is healed.

Turning now to FIG. 8, there is shown a schematic representation of an uncoupled assembly of coupling members located in a sectioned colon. While the assembly is shown in conjunction with colon repair, it should be understood that use of the assembly is equally applicable for the repair of other tubular structures such as the large and small bowel and the esophagus to name but a few. Colon 70 having wall portions 72, 74 and free ends 76, 78, is shown having an assembly implanting device 80 located therein. Device 80, in one end of colon 70, supports coupling member 12 at the end of central portion 82 engaging a knob portion 84. In the other end of colon 70, device 80 supports coupling members 22, 32 and a cutting blade 86. During assembly installation, ends 76, 78 are gathered against central portion 82 of device 80, the three coupling members are urged into contact and pressed into full locking engagement, cutting blade 86 is advanced to cut the ends 76, 78 and then to cut member 12 along and through the inner face of surface 16 at the location of recess 18, and thereafter device 80 is withdrawn through colon 70 leaving the assembly as shown in FIG. 9. The anastomosis will heal in and about the region designated 88 and thereafter the assembly will naturally be expelled intact by the patient leaving colon 70, at the anastomatic site, with an open passageway substantially like that which existed before resectioning.

Next turning to FIG. 10, there is schematically depicted coupling member 12 substantially as provided in FIG. 2A. However, projecting segment 21 includes a land 23 for receiving in locking engagement therewith projection 36 of coupling member 32. Also, one might observe that the end of each projecting segment 21 has been turned for ease in installation when segment 21 passes between coupling members 22 and 32 during member assembly.

Upon viewing FIG. 11, there is schematically depicted coupling members 22 and 32 substantially as provided in FIG. 2. However, the land, now designated 30', is located on member 32 instead of on member 22 and the projection, now designated 36', is located on member 22 instead of the member 32. The coupling of the members to form the assembly is accomplished as heretofore indicated.

Lastly, FIG. 12 depicts coupling member 48 substantially as illustrated in FIG. 5. However, the recess has now been designated 52' and follows a spiral pathway traversing a full revolution. The arrows show the spiral path. FIG. 13 illustrates a developed view of the spiral of FIG. 12.

While in accordance with provisions of the statutes there is described herein a specific embodiment of the invention, those skilled in the art will understand that changes may be made in the form of the invention covered by the claims appended hereto without departing from the scope and spirit thereof, and that certain features of the invention may sometimes be used to an advantage without corresponding use of the other features.

I claim:

1. An assembly for compression anastomosis of a tubular structure comprising a first, a second and a third coupling member each being generally a hollow open cylinder, said first coupling member being dimensioned and configured to receive therein at least a portion of said second coupling member with said second coupling member being dimensioned and configured to receive therein at least a portion of said third coupling member, and means disposed on said portion of said second coupling member adapted for locking coaction with complementary means disposed proximate a first end of said portion of said third coupling member, with each said coupling member being aligned and urged into engagement, said third coupling member forces said portion of said second coupling member into locking engagement with said first coupling member, with said first end of said third coupling member mechanically locking within said portion of said second coupling member thereby effecting an assembly of interlocking coupling members.

2. An assembly for compression anastomosis of a tubular structure comprising
a first coupling member being generally a thin wall hollow cylinder having first and second ends with the second end being open and the first end having a surface;
a second coupling member being generally a thin wall hollow cylinder having open first and second ends and including a first portion;
a third coupling member being generally a thin wall hollow cylinder having open first and second ends;
said first coupling member being dimensioned and configured to receive therein said first portion of said second coupling member with said second coupling member being dimensioned and configured to receive therein at least a portion of said third coupling member; and
means disposed on said first portion of said second coupling member adapted for locking coaction with complementary means disposed proximate a first end of said third coupling member,
with each said coupling member being aligned and urged into engagement, said third coupling member forces said first portion of said second coupling member into locking engagement with said first coupling member, with said first end of said third coupling member mechanically locking within said first portion of said second coupling member thereby effecting an assembly of interlocking coupling members.

3. The assembly according to claim 2 wherein said first portion means is a land and said complementary means is a projection.

4. The assembly according to claim 2 wherein said first portion means is a projection and said complementary means is a land.

5. The assembly according to claim 2 further including means for guiding a cutting instrument adapted for usage with said assembly during assembly installation.

6. The assembly according to claim 5 wherein said means is a rib disposed on an inner face of said surface.

7. The assembly according to claim 5 wherein said means is an annular bevel disposed on an inner face of said surface.

8. The assembly according to claim 2 further including means disposed on the inner face of said surface for latching engagement with an instrument adapted for usage during assembly installation.

9. The assembly according to claim 2 further including a recess disposed in said surface.

10. An assembly for compression anastomosis of a tubular structure comprising
a first coupling member being generally a thin wall hollow cylinder having first and second ends with the second end being open and the first end having a surface with an axial port;
a second coupling member being generally a thin wall hollow cylinder having open first and second ends and including a first portion having one or more openings disposed in the wall;
a third coupling member being generally a thin wall hollow cylinder having open first and second ends;
said first coupling member being dimensioned and configured to receive therein said first portion of said second coupling member with said second coupling member being dimensioned and configured to receive therein at least a portion of said third coupling member; and
means disposed on said first portion of said second coupling member adapted for locking coaction with complementary means disposed proximate a first end of said third coupling member,
with each said coupling member being aligned and urged into engagement, said third coupling member forces said first portion of said second coupling member into locking engagement with said first coupling member, with said first end of said third coupling member mechanically locking within said first portion of said second coupling member thereby effecting an assembly of interlocking coupling members.

11. The assembly according to claim 10 wherein said first portion means is a land and said complementary means is a projection.

12. The assembly according to claim 10 wherein said first portion means is a projection and said complementary means is a land.

13. The assembly according to claim 10 further including a recess disposed in said surface.

14. The assembly according to claim 13 wherein said recess is disposed on an outer face of said surface.

15. The assembly according to claim 13 wherein said recess is disposed on an inner face of said surface.

16. The assembly according to claim 13 wherein said recess comprises at least one continuous channel.

17. The assembly according to claim 16 wherein said channel follows a spiral path.

18. The assembly according to claim 16 wherein said channel follows an angular path.

19. The assembly according to claim 10 further including means for guiding a cutting instrument adapted for usage with said assembly during assembly installation.

20. The assembly according to claim 19 wherein said means is a rib disposed on an inner face of said surface.

21. The assembly according to claim 19 wherein said means is an annular bevel disposed on an inner face of said surface.

22. The assembly according to claim 10 wherein said surface further includes one or more openings disposed therein forming a spoke-like configuration.

23. An assembly for compression anastomosis of a tubular structure comprising a first, a second and a third coupling member each being generally a hollow open cylinder, said first coupling member being dimensioned and configured to receive therein at least a portion of said second coupling member with said second coupling member being dimensioned and configured to receive therein at least a portion of said third coupling member, and means for mechanically locking together said coupling members, said mechanical locking means including at least one projecting segment disposed on said first coupling member adapted for locking coaction with said third coupling member, means disposed on a first portion of said second coupling member adapted for locking coaction with complementary means disposed proximate a first end of said third coupling member, with each said coupling member being aligned and urged into engagement, said coupling members mechanically latch to thereby effect an assembly of interlocking coupling members.

24. The assembly according to claim 23 wherein said projecting segment passes through said third coupling member latching proximate an end of said third coupling member.

25. An assembly for compression anastomosis of a tubular structure comprising a first, a second and a third coupling member each being generally a hollow open cylinder, said first coupling member being dimensioned and configured to receive therein at least a portion of said second coupling member with said second coupling member being dimensioned and configured to receive therein at least a portion of said third coupling member, and means for mechanically locking together said coupling members, said mechanical locking means including at least one projecting segment disposed on said first coupling member adapted for passage between said second and said third coupling members for latching proximate an end of said third coupling member, means disposed on a first portion of said third coupling member adapted for locking coaction with complementary means disposed on said projecting segment, with each said coupling member being aligned and urged into engagement, said coupling members mechanically latch to thereby effect an assembly of interlocking coupling members.

26. The assembly according to claim 25 wherein said projecting segment latches proximate an end of said second coupling member.

* * * * *